United States Patent
Murayama et al.

(10) Patent No.: US 8,742,164 B2
(45) Date of Patent: Jun. 3, 2014

(54) METHOD FOR PRODUCING TOLUENEDICARBAMATE, METHOD FOR PRODUCING TOLUENEDIISOCYANATE, AND TOLUENEDICARBAMATE

(75) Inventors: Koichi Murayama, Chiba (JP); Yoshiki Shimokawatoko, Chiba (JP); Takashi Kanno, Ichihara (JP); Koji Takamatsu, Ichihara (JP); Hiroshi Takeuchi, Ichihara (JP); Masaaki Sasaki, Ichihara (JP); Yasushi Kotaki, Tokyo (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 13/807,979

(22) PCT Filed: May 19, 2011

(86) PCT No.: PCT/JP2011/061516
§ 371 (c)(1),
(2), (4) Date: Jan. 2, 2013

(87) PCT Pub. No.: WO2012/005059
PCT Pub. Date: Jan. 12, 2012

(65) Prior Publication Data
US 2013/0109881 A1   May 2, 2013

(30) Foreign Application Priority Data
Jul. 7, 2010   (JP) ................... 2010-154825

(51) Int. Cl.
*C07C 261/00* (2006.01)

(52) U.S. Cl.
USPC .......................................... 560/158

(58) Field of Classification Search
USPC ................................. 560/158, 27
See application file for complete search history.

(56) References Cited

U.S. PATENT DOCUMENTS

| 4,430,505 A |   | 2/1984 | Heitkamper et al. |
| 4,611,079 A | * | 9/1986 | Merger et al. ................ 560/25 |

FOREIGN PATENT DOCUMENTS

| CA | 1144562 |   | 4/1983 |
| CN | 1488623 | A | 4/2004 |
| EP | 0 437 258 | A1 | 9/1991 |
| JP | 56-103152 |   | 8/1981 |
| JP | 57-114561 |   | 7/1982 |
| JP | 4-18064 |   | 1/1992 |

OTHER PUBLICATIONS

International Search Report PCT/JP2011/061516 dated Aug. 16, 2011.

* cited by examiner

*Primary Examiner* — Wu-Cheng Winston Shen
*Assistant Examiner* — Blaine G Doletski
(74) *Attorney, Agent, or Firm* — Foley & Lardner LLP (57) ABSTRACT

A method for producing toluenedicarbamate includes a carbamate production process of producing toluenedicarbamate by reaction between toluenediamine, urea, and/or N-unsubstituted carbamic acid ester, and alcohol; and a benzoyleneurea reduction process of reducing a disubstituted benzoyleneurea and a derivative thereof to 10 mol or less relative to 100 mol of toluenedicarbamate, wherein the disubstituted benzoyleneurea is represented by formula (1) below and has a methyl group and an amino group:

[Chemical Formula 1]

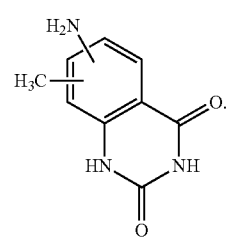

(1)

11 Claims, 1 Drawing Sheet

METHOD FOR PRODUCING TOLUENEDICARBAMATE, METHOD FOR PRODUCING TOLUENEDIISOCYANATE, AND TOLUENEDICARBAMATE

TECHNICAL FIELD

The present invention relates to a method for producing toluenedicarbamate, a method for producing toluenediisocyanate, and toluenedicarbamate.

BACKGROUND ART

Heretofore, carbamates (urethane compounds) such as alkyl carbamates have been useful organic compounds as an industrial raw material having a wide variety of use, including a raw material for medical and pharmaceutical products, agrochemicals, etc.; a raw material for various fine chemicals; and also as an analysis reagent for alcohols.

Also, various examinations have recently been conducted on use of such alkylcarbamate as a raw material for phosgene-free isocyanate production.

Isocyanate is an organic compound containing an isocyanate group, used widely as a raw material for polyurethane, and industrially, produced by reaction between amine and phosgene (phosgene method).

However, phosgene is highly toxic and corrosive, and its handling is troublesome. Therefore, recently, as an economic method of isocyanate production that can replace the phosgene method has been proposed: in the method, carbamate is produced by reaction between amine, urea or carbamic acid ester, and alcohol, and thereafter, isocyanate is produced by thermal decomposition of the obtained carbamate.

As an example of such a carbamate production method, Example 11 of Patent Document 1 below has proposed obtaining 2,4-bis-(n-hexoxycarbonyl-amino)-toluene by reaction between diaminotoluene, urea, and n-hexanol in the presence of a Lewis acid catalyst.

CITATION LIST

Patent Document

Patent Document 1
Japanese Unexamined Patent Publication No. Sho 57-114561

SUMMARY OF THE INVENTION

Problem to be Solved by the Invention

However, when isocyanate is produced by thermally decomposing the carbamate (2,4-bis-(n-hexoxycarbonyl-amino)-toluene) obtained by the above-described method, in the thermal decomposition, the above-described carbamate and isocyanate, or intermediates thereof may cause unpreferable polymerization reaction such as multimerization, biuretization, or allophanatization in some cases. In particular, as in the case of the above-described 2,4-bis-(n-hexoxycarbonyl-amino)-toluene, when the carbamate or its intermediate has an amino group, it has been known that the amino group and isocyanate cause unpreferable reactions.

When such a reaction is caused, there are disadvantages such as the following: solid content residues are produced in a large amount as a by-product, and the residue causes blockage of the isocyanate production system, and decrease production efficiency of isocyanate.

An object of the present invention is to provide a method for producing toluenedicarbamate, with which production of by-products can be reduced; toluenedicarbamate obtained by such a production method; and a method for producing toluenediisocyanate in which the toluenedicarbamate is used for production of toluenediisocyanate.

Means for Solving the Problem

A method for producing toluenedicarbamate of the present invention includes
a carbamate production process of producing toluenedicarbamate by reaction between toluenediamine, urea and/or N-unsubstituted carbamic acid ester, and alcohol; and
a benzoyleneurea reduction process of reducing a disubstituted benzoyleneurea and a derivative thereof to 10 mol or less relative to 100 mol of toluenedicarbamate,
wherein the disubstituted benzoyleneurea is represented by formula (1) below and has a methyl group and an amino group:

[Chemical Formula 1]

(1)

In the method for producing toluenedicarbamate of the present invention, it is preferable that the benzoyleneurea reduction process includes a biuret compound reduction process of reducing a biuret compound represented by formula (2) below to 40 mol or less relative to 100 mol of toluenediamine:

$$X_1\text{—CO—NH—CO—}X_2 \quad (2)$$

(where $X_1$ and $X_2$ may be the same or different from each other, and represent an amino group, an alkoxy group, or an N-(aminotoluyl)amino group).

In the method for producing toluenedicarbamate of the present invention, it is preferable that the biuret compound reduction process includes a first biuret compound reduction process of reducing a first biuret compound represented by formula (2) above where $X_1$ and $X_2$ are amino groups.

In the method for producing toluenedicarbamate of the present invention, it is preferable that the method further includes a urea feeding process of feeding urea to the carbamate production process,
wherein in the first biuret compound reduction process,
when the urea feeding process includes a fluid feeding process, in which urea is melted by heating to be in a fluid state, and to be fed to the carbamate production process, the time after the melting of urea to the completion of its feeding is set to within 2 hours,
in the urea feeding process, urea is fed as a slurry to the carbamate production process or
in the urea feeding process, urea is fed in a solid state to the carbamate production process.

In the method for producing toluenedicarbamate of the present invention, it is preferable that the biuret compound reduction process includes a second biuret compound reduction process of reducing a second biuret compound represented by formula (2) above where $X_1$ is an amino group or an alkoxy group and $X_2$ is an alkoxy group.

In the method for producing toluenedicarbamate of the present invention, it is preferable that the method further includes an N-unsubstituted carbamic acid ester production process of producing N-unsubstituted carbamic acid ester by reaction between the urea and alcohol, wherein in the second biuret compound reduction process, urea and alcohol are allowed to react in the presence of a metal-containing compound in the N-unsubstituted carbamic acid ester production process.

In the method for producing toluenedicarbamate of the present invention, it is preferable that the biuret compound reduction process includes a third biuret compound reduction process of reducing a third biuret compound represented by formula (2) above where $X_1$ is an N-(aminotoluyl)amino group, and $X_2$ is any of an amino group, an alkoxy group, and an N-(aminotoluyl)amino group.

In the method for producing toluenedicarbamate of the present invention, it is preferable that in the third biuret compound reduction process, in the carbamate production process, ammonia by-produced in the reaction is reduced from the reaction system; the reaction temperature is set to 160° C. or more; or 2 mol or more of alcohol relative to 1 mol of toluenediamine is fed.

In the method for producing toluenedicarbamate of the present invention, it is preferable that the carbamate production process is performed in a reaction apparatus including a reaction tank, a reflux line for refluxing a low boiling component drained from the reaction tank, and a separator provided in the reflux line for separating a reflux component and a drain component, and when the third biuret compound reduction process is a process of reducing ammonia by-produced in the reaction from the reaction system in the carbamate production process, the reaction tank is purged with nitrogen;

a condenser is used as the separator, and the temperature of the condenser is set to 40° C. or more to suppress condensation of ammonia; or a distiller is used as the separator, and distillation is performed so that the amount of ammonia contained in the drain component is larger than the amount of ammonia contained in the reflux component.

A method for producing toluenediisocyanate of the present invention includes a toluenedicarbamate producing process of the above-described method for producing toluenedicarbamate, and a toluenediisocyanate producing process of thermally decomposing the produced toluenedicarbamate.

Toluenedicarbamate of the present invention is a toluenedicarbamate, and contains, as an impurity, 0.01 to 10 mol of a disubstituted benzoyleneurea and a derivative thereof relative to 100 mol of toluenedicarbamate, wherein the disubstituted benzoyleneurea is represented by formula (1) below and has a methyl group and an amino group:

[Chemical Formula 2]

(1)

Effects of the Invention

Usually, when toluenediamine, urea and/or N-unsubstituted carbamic acid ester, and alcohol are allowed to react, while the raw material components produce toluenedicarbamate, the same raw material components produce also the disubstituted benzoyleneurea represented by formula (1) above, and therefore this is disadvantageous because it reduces production efficiency of toluenedicarbamate.

However, the method for producing toluenedicarbamate of the present invention includes a benzoyleneurea reduction process, and therefore the disubstituted benzoyleneurea and a derivative thereof are reduced to 10 mol or less relative to 100 mol of toluenedicarbamate.

Therefore, with the method for producing toluenedicarbamate of the present invention, toluenedicarbamate can be produced with excellent efficiency.

Furthermore, with the method for producing toluenedicarbamate of the present invention, the carbamate intermediate having an amino group is reduced, and therefore in the method for producing toluenediisocyanate of the present invention, reaction of such a carbamate intermediate having an amino group with isocyanate can be reduced, thereby achieving reduction in residues (solid content) obtained as by-products.

As a result, with the method for producing toluenediisocyanate of the present invention, blockage of the production system is suppressed, and isocyanate can be produced with excellent yields.

EMBODIMENT OF THE INVENTION

A method for producing toluenedicarbamate of the present invention includes a carbamate production process and a benzoyleneurea reduction process.

The carbamate production process is a process of producing toluenedicarbamate. To be specific, in this process, toluenediamine, urea and/or N-unsubstituted carbamic acid ester, and alcohol are allowed to react, to produce toluenedicarbamate.

Toluenediamine (also called: tolylenediamine, diaminotoluene) is not particularly limited, and toluenediamine with various patterns of substitution sites may be used. Industrially, preferably, 2,4-toluenediamine (2,4-tolylenediamine, 2,4-diaminotoluene), or 2,6-toluenediamine (2,6-tolylenediamine, 2,6-diaminotoluene) is used.

These toluenediamines may be used singly or in a combination of two or more.

Urea is not particularly limited, and those generally and commercially available ureas may be used. Ureas can also be produced separately and used.

Figure 1:
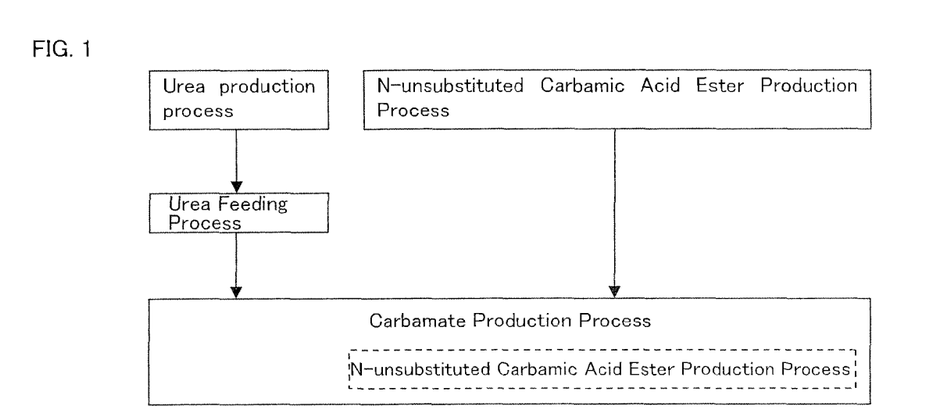
FIG. 1 is a schematic view illustrating an embodiment of a carbamate production process, when a first biuret compound reduction process and a second biuret compound reduction process are included.

In the method for producing toluenedicarbamate of the present invention, for example, a urea production process of producing urea from ammonia and carbon dioxide is included, and the urea produced in the urea production process is fed as a raw material component to the carbamate production process (ref: FIG. 1).

In FIG. 1, the urea produced in the urea production process is solid at normal temperature, and therefore in order to feed the urea industrially to the carbamate production process, in a urea feeding process, for example, the produced urea is heated, for example, at 135° C. or more, preferably 180° C. or less so that the urea is melted; and the urea in a fluid state is transported (fed) from the urea production process (urea production tank) to the carbamate production process (reaction tank), via a pipe connected therebetween (fluid feeding process).

To produce urea in the urea production process, for example, first, as shown in formula (3) below, ammonia and carbon dioxide (carbon dioxide gas) are allowed to react to produce ammonium carbamate.

$$2NH_3 + CO_2 \rightarrow NH_2COONH_4 \quad (3)$$

Reaction between ammonia and carbon dioxide can be performed by a known method, and the reaction conditions thereof (mixing formulation, temperature, pressure, etc.) are set suitably in accordance with purpose and application.

Next, in this method, as shown in formula (4) below, the obtained ammonium carbamate is subjected to dehydration, thereby decomposing the ammonium carbamate into urea and water.

$$NH_2COONH_4 \rightarrow NH_2CONH_2 + H_2O \quad (4)$$

The dehydration of ammonium carbamate can be performed by a known method, and the reaction conditions thereof (temperature, pressure, etc.) are set suitably in accordance with purpose and application.

The N-unsubstituted carbamic acid ester is a carbamic acid ester in which a nitrogen atom of a carbamoyl group is not substituted with a functional group (i.e., the nitrogen atom is bonded to two hydrogen atoms and one carbon atom), and is represented, for example, by general formula (5) below:

$$RO-CO-NH_2 \quad (5)$$

(where R represents an alkyl group, or an aryl group which may have a substituent).

In formula (5) above, R represents an alkyl group, or an aryl group which may have a substituent.

Examples of the alkyl group represented by R in formula (5) above include: a linear or branched saturated hydrocarbon group having 1 to 8 carbon atoms such as methyl, ethyl, n-propyl, iso-propyl, n-butyl, iso-butyl, sec-butyl, tert-butyl, pentyl, hexyl, heptyl, octyl, iso-octyl, and 2-ethylhexyl; and an alicyclic saturated hydrocarbon group having 5 to 10 carbon atoms such as cyclohexyl and cyclododecyl.

As the alkyl group represented by R, it is preferable to use a linear or branched saturated hydrocarbon group having 1 to 8 carbon atoms, more preferably a linear or branched saturated hydrocarbon group having 2 to 6 carbon atoms, or even more preferably a linear saturated hydrocarbon group having 2 to 6 carbon atoms.

Examples of the N-unsubstituted carbamic acid ester in which R represents an alkyl group in formula (5) above include: N-unsubstituted carbamic acid esters containing a saturated hydrocarbon such as methyl carbamate, ethyl carbamate, n-propyl carbamate, iso-propyl carbamate, n-butyl carbamate, iso-butyl carbamate, sec-butyl carbamate, tert-butyl carbamate, pentyl carbamate, hexyl carbamate, heptyl carbamate, octyl carbamate, iso-octyl carbamate, and 2-ethylhexyl carbamate; and N-unsubstituted carbamic acid esters containing an alicyclic saturated hydrocarbon such as cyclohexyl carbamate and cyclododecyl carbamate.

Examples of the aryl group which may have a substituent, represented by R in formula (5) above, include aryl groups having 6 to 18 carbon atoms such as phenyl, tolyl, xylyl, biphenyl, naphthyl, anthryl, and phenanthryl. Examples of the substituent include a hydroxyl group, a halogen atom (e.g., chlorine, fluorine, bromine, and iodine), a cyano group, an amino group, a carboxyl group, an alkoxy group (e.g., an alkoxy group having 1 to 4 carbon atoms such as a methoxy, an ethoxy, a propoxy, or a butoxy group), an aryloxy group (e.g., a phenoxy group etc.), an alkylthio group (e.g., an alkylthio group having 1 to 4 carbon atoms such as a methylthio, an ethylthio, a propylthio, or a butylthio group), and an arylthio group (e.g., a phenylthio group). When the substituents are multiply substituted at the aryl group, the substituents may be the same or different from each other.

Examples of the N-unsubstituted carbamic acid ester in which R represents an aryl group which may have a substituent in formula (5) above include N-unsubstituted carbamic acid esters containing an aromatic hydrocarbon such as phenyl carbamate, tolyl carbamate, xylyl carbamate, biphenyl carbamate, naphthyl carbamate, anthryl carbamate, and phenanthryl carbamate.

These N-unsubstituted carbamic acid esters can be used alone or in a combination of two or more.

As the N-unsubstituted carbamic acid ester, it is preferable to use N-unsubstituted carbamic acid ester in which R represents an alkyl group in formula (5) above.

Such an N-unsubstituted carbamic acid ester can be produced, for example, by allowing the raw material components, i.e., urea and alcohol (ROH represented by general formula (7) to be described later), to react in the reaction system (reaction tank) of the carbamate production process, as shown in formula (6) below (ref: broken line in FIG. 1, N-unsubstituted carbamic acid ester production process).

$$NH_2CONH_2 + ROH \rightarrow NH_2COOR + NH_3 \quad (6)$$

Alternatively, the raw material component of urea and alcohol are allowed to react in advance as shown in formula (6) above to produce N-unsubstituted carbamic acid ester (ref: solid line in FIG. 1, N-unsubstituted carbamic acid ester production process), and the produced N-unsubstituted carbamic acid ester can be fed to the carbamate production process.

The alcohol is, for example, a primary to tertiary monohydric alcohol and is, for example, represented by general formula below (7):

$$R-OH \quad (7)$$

(where R is as defined for R in formula (5) above).

In formula (7) above, R is as defined for R in formula (5) above, or in other words, represents an alkyl group, or an aryl group which may have a substituent.

Examples of the alcohol in which R represents the alkyl group in formula (7) above include: alcohols containing a linear or branched saturated hydrocarbon, such as methanol, ethanol, n-propanol, iso-propanol, n-butanol (1-butanol), iso-butanol, sec-butanol, tert-butanol, pentanol, hexanol, heptanol, octanol, iso-octanol, and 2-ethylhexanol; and alcohols containing an alicyclic saturated hydrocarbon, such as cyclohexanol and cyclododecanol.

Examples of the alcohol in which R represents the above-described aryl group which may have a substituent in formula (7) above include phenol, hydroxytoluene, hydroxyxylene, biphenyl alcohol, naphthalenol, anthracenol, and phenanthrenol.

These alcohols can be used alone or in a combination of two or more.

As the alcohol, in formula (7) above, it is preferable to use an alcohol in which R represents an alkyl group, more preferably an alcohol in which R represents an alkyl group having 1 to 8 carbon atoms, or even more preferably an alcohol in which R represents an alkyl group having 2 to 6 carbon atoms.

Then, in this method, the above-described toluenediamine, urea and/or N-unsubstituted carbamic acid ester, and alcohol are mixed, and preferably, the mixture is allowed to react in a liquid phase.

The amounts of the mixed toluenediamine, urea and/or N-unsubstituted carbamic acid ester, and alcohol are not particularly limited and can be appropriately selected over a relatively wide range.

Usually, the amounts of the urea and/or N-unsubstituted carbamic acid ester, and the amount of the alcohol may be equimolar or more to the amount of the amino group in the toluenediamine, so that the urea and/or the N-unsubstituted carbamic acid ester, and the alcohol themselves can also be used as reaction solvents in this reaction.

When the urea and/or N-unsubstituted carbamic acid ester, and alcohol also serve as the reaction solvents, as necessary, excess amounts of the urea and/or the N-unsubstituted carbamic acid ester and the alcohol are used. Large excess amounts thereof, however, increase consumption energy in the separation step after the reaction, which may be unsuitable for industrial production.

Therefore, from the viewpoint of improving the yield of the carbamate, the amount(s) of the urea and/or the N-unsubstituted carbamic acid ester is/are of the order of 1 to 20 times moles, preferably 1 to 10 times moles, or more preferably 1 to 5 times moles with respect to one amino group of the toluenediamine, and the amount of the alcohol is of the order of 1 to 100 times moles, preferably 1 to 20 times moles, or more preferably 1 to 10 times moles, with respect to one amino group of the toluenediamine.

In this reaction, although a reaction solvent is not necessarily required, for example, when reaction raw materials are solid or when a reaction product is deposited, blending of a reaction solvent such as aliphatic hydrocarbons, aromatic hydrocarbons, ethers, nitriles, aliphatic halogenated hydrocarbons, amides, nitro compounds, N-methyl pyrrolidinone, N,N-dimethylimidazolidinone, dimethyl sulfoxide can improve operability.

The amount of the reaction solvent is not particularly limited as long as it is sufficient for the carbamate as a desired product to be dissolved. Industrially, the amount of the reaction solvent is preferably reduced as much as possible because it is necessary to recover the reaction solvent from the reaction solution and reduce the energy consumed for the recovery as much as possible, and also because a large amount of the reaction solvent can decrease substrate concentration on the reaction and slow the reaction rate. More specifically, the amount of the reaction solvent is usually in the range of 0 to 500 parts by mass, or preferably 0 to 100 parts by mass, per 1 part by mass of the toluenediamine.

In this reaction, the reaction temperature is appropriately selected from the range of 100 to 350° C., or preferably 150 to 300° C. When the reaction temperature is lower than this range, the reaction rate may decrease. On the other hand, when the reaction temperature is higher than this range, a side reaction increases, so that the yield of the carbamate as a desired product may be reduced.

The reaction is usually carried out under atmospheric pressure. However, when the boiling point of the component in the reaction solution is lower than the reaction temperature, the reaction may be carried out under an increased pressure or, if necessary, under a reduced pressure.

The reaction time is in the range of, for example, 0.1 to 20 hours, or preferably 0.5 to 10 hours. When the reaction time is shorter than this range, the yield of the carbamate as a desired product may be reduced. On the other hand, when the reaction time is longer than this range, the reaction is unsuitable for industrial production.

In this method, a catalyst can also be used.

There is no particular limitation on the catalyst, and examples thereof include lithium methanolate, lithium ethanolate, lithium propanolate, lithium butanolate, sodium methanolate, potassium-tert-butanolate, magnesium methanolate, calcium methanolate, tin (II) chloride, tin (IV) chloride, lead acetate, lead phosphate, antimony (III) chloride, antimony (V) chloride, aluminum acetylacetonate, aluminum-isobutylate, aluminum trichloride, bismuth (III) chloride, copper (II) acetate, copper (II) sulfate, copper (II) nitrate, bis(triphenyl-phosphinoxide)-copper (II) chloride, copper molybdate, silver acetate, gold acetate, zinc oxide, zinc chloride, zinc acetate, zinc acetonylacetate, zinc octanoate, zinc oxalate, zinc hexylate, zinc benzoate, zinc undecylenate, cerium (IV) oxide, uranyl acetate, titanium tetraisopropanolate, titanium tetrabutanolate, titanium tetrachloride, titanium tetraphenolate, titanium naphthenate, vanadium (III) chloride, vanadium acetylacetonate, chromium (III) chloride, molybdenum (VI) oxide, molybdenum acetylacetonate, tungsten (VI) oxide, manganese (II) chloride, manganese (II) acetate, manganese (III) acetate, iron (II) acetate, iron (III) acetate, iron phosphate, iron oxalate, iron (III) chloride, iron (III) bromide, cobalt acetate, cobalt chloride, cobalt sulfate, cobalt naphthenate, nickel chloride, nickel acetate, and nickel naphthenate.

Furthermore, examples of the catalyst include $Zn(OSO_2CF_3)_2$ (also known as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

These catalysts can be used singly or in a combination of two or more.

The amount of the catalyst is in the range of, for example, 0.000001 to 0.1 mol, or preferably 0.00005 to 0.05 mol, per 1 mol of the toluenediamine. Even if the amount of the catalyst is more than the above range, no further remarkable reaction enhancing effect is observed, and at the same time, cost may increase due to an increase in the amount. On the other hand, when the amount is less than the above range, the reaction enhancing effect may not be obtained.

The method for adding the catalyst is not particularly limited, and any of package addition, continuous addition, and intermittent addition in portions can be used.

Then, this reaction may be carried out, for example, by introducing the toluenediamine, urea and/or N-unsubstituted carbamic acid ester, alcohol, and if necessary, a catalyst and a reaction solvent, in a reaction tank under the above-described conditions, and stirring or mixing the mixture.

In this reaction, either of a batch reaction process or a continuous reaction process can be adopted.

The reaction progresses, for example, as shown in formula (8) below, and produces, as a main product, for example, toluenedicarbamate represented by the general formula (9) below:

[Chemical Formula 3]

(8)

[Chemical Formula 4]

(9)

(where R is as defined for R in formula (5) above).

Examples of the toluenedicarbamate include, in accordance with the toluenediamine of the raw material component, 2,4-toluenedicarbamate, 2,6-toluenedicarbamate, and a mixture thereof.

Also, in this reaction, a gas containing alcohol (excess raw material alcohol), ammonia, and carbon dioxide is by-produced as a drained gas.

Furthermore, in this reaction, as described above, by reaction of urea and alcohol, sometimes excess N-unsubstituted carbamic acid ester, and carbonates (e.g., dialkylcarbonate, diarylcarbonate, alkylarylcarbonate, etc.) are also by-produced as low boiling components.

Furthermore, in this reaction, as by-products, a disubstituted benzoyleneurea (1,2,3,4-tetrahydroquinazoline-2,4-dione) having a methyl group and an amino group and a derivative thereof are produced.

Such a disubstituted benzoyleneurea is, to be specific, represented by formula (1) below:

[Chemical Formula 5]

(1)

Examples of the derivative of the disubstituted benzoyleneurea include a carbamate derivative represented by formula (10) below where the amino group in the disubstituted benzoyleneurea is replaced with carbamic acid ester:

[Chemical Formula 6]

(10)

(where R is as defined for R in formula (5) above).

In the formulas below, the derivative of the disubstituted benzoyleneurea is omitted, and only the disubstituted benzoyleneurea is shown.

That is, when toluenediamine, urea and/or N-unsubstituted carbamic acid ester, and alcohol are allowed to react, the above-described toluenedicarbamate is obtained, and also excess (unreacted) alcohol, excess (unreacted) urea and/or N-unsubstituted carbamic acid ester, carbonate, are obtained as low boiling components, and furthermore, disubstituted benzoyleneurea and a derivative thereof are obtained.

In such a case, the low boiling components can be refluxed, as necessary, by a known method, and can be effectively used in the above-described reaction. However, when the disubstituted benzoyleneurea and a derivative thereof are produced, it is disadvantageous in that production efficiency of toluenedicarbamate decreases. Thus, in this method, the above-described disubstituted benzoyleneurea and a derivative thereof are reduced to 10 mol or less, preferably 5 mol or less relative to 100 mol of toluenedicarbamate (benzoyleneurea reduction process).

In the benzoyleneurea reduction process, the disubstituted benzoyleneurea and a derivative thereof can be reduced by the following method. For example, the produced disubstituted benzoyleneurea and a derivative thereof can be directly removed, or preferably, various intermediates (intermediate products) in the reaction that produce the disubstituted benzoyleneurea and a derivative thereof are removed (reduced). The disubstituted benzoyleneurea and a derivative thereof can be reduced in this manner.

The reaction pathway that produces the disubstituted benzoyleneurea and a derivative thereof by reaction between toluenediamine, urea and/or N-unsubstituted carbamic acid ester, and alcohol, is variously examined, as described later. Examples of the intermediate (the intermediate product in the reaction that produces the disubstituted benzoyleneurea and a derivative thereof) include a biuret compound represented by formula (2) below (biuret or a derivative thereof):

$$X_1\text{—CO—NH—CO—}X_2 \quad (2)$$

(where $X_1$ and $X_2$ may be the same or different from each other, and represent an amino group, an alkoxy group, or an N-(aminotoluyl) amino group).

Thus, in this method, to reduce the disubstituted benzoyleneurea and a derivative thereof, the biuret compound represented by formula (2) above is reduced to, for example, 40 mol or less, preferably 20 mol or less relative to 100 mol of toluenediamine (biuret compound reduction process).

Examples of the biuret compound reduced in the biuret compound reduction process include, to be more specific, a first biuret compound represented by formula (2) above where $X_1$ and $X_2$ are amino groups (ref: formula (11) below); a second biuret compound represented by formula (2) above where $X_1$ is an amino group or an alkoxy group and $X_2$ is an alkoxy group (ref: formula (12A) and formula (12B) below); and a third biuret compound represented by formula (2) above where $X_1$ is an N-(aminotoluyl) amino group represented by formula (13) below, and $X_2$ is any of an amino group, an alkoxy group, or an N-(aminotoluyl) amino group represented by formula (13) below.

Examples of the third biuret compound include, to be more specific, a third biuret compound (ref: formula (14) below) represented by formula (2) above where $X_1$ is an N-(aminotoluyl) amino group and $X_2$ is an amino group; a third biuret compound (ref: formula (15) below) represented by formula (2) above where $X_1$ is an N-(aminotoluyl) amino group and $X_2$ is an alkoxy group; and a third biuret compound (ref: formula (16) below) represented by formula (2) above where $X_1$ and $X_2$ are N-(aminotoluyl) amino groups.

[Chemical Formula 7]

(11)

[Chemical Formula 8]

(12A)

[Chemical Formula 9]

(12B)

[Chemical Formula 10]

(13)

[Chemical Formula 11]

(14)

[Chemical Formula 12]

(15)

[Chemical Formula 13]

(16)

Thus, the biuret compound reduction process includes, for example, a first biuret compound reduction process in which above-described first biuret compound is reduced; a second biuret compound reduction process in which the above-described second biuret compound is reduced; and a third biuret compound reduction process in which the above-described third biuret compound is reduced.

FIG. 1 is a schematic view illustrating an embodiment of a carbamate production process, when the first biuret compound reduction process and the second biuret compound reduction process are included.

In the following, the first biuret compound reduction process and the second biuret compound reduction process are described with reference to FIG. 1.

[First Biuret Compound Reduction Process]

As an example of the reaction pathway, in which the first biuret compound represented by formula (11) above is produced as an intermediate from the above-described raw material components and further the disubstituted benzoyleneurea and a derivative thereof are produced from the first biuret compound, to be specific, a reaction pathway represented by formula (17) below may be used.

[Chemical Formula 14]

(17)

In such reactions, for example, urea is dimerized to produce the first biuret compound (biuret), and by addition of toluenediamine to the first biuret compound, the disubstituted benzoyleneurea and a derivative thereof are produced.

To suppress such a reaction, the dimerization of the urea is suppressed to reduce the first biuret compound production.

Thus, when the method for producing toluenedicarbamate of the present invention includes the above-described urea feeding process in which urea is fed to the carbamate production process, as shown in FIG. 1, in the first biuret compound reduction process, (1) when, in the urea feeding process, urea is melted by heating to be in a fluid state, and then fed to the carbamate production process (that is, when the fluid feeding process is included), the time it takes from the completion of melting of urea to the completion of the feeding (time required for the fluid feeding process) is set to, for example, within 2 hours, preferably within 1 hour.

With such a first biuret compound reduction process, urea is fed to the carbamate production process with a reduced heating time for allowing urea to be in a melted state. Therefore, dimerization of urea is suppressed, and the first biuret compound can be reduced.

Alternatively, in the urea feeding process, urea can be fed as follows, for example, without being melted by heating to be in a fluid state (that is, without including the fluid feeding process):

(2) urea can be fed as a slurry to the carbamate production process, or (3) urea can be fed as is in a solid state to the carbamate production process.

With such a first biuret compound reduction process (above-described (2) and (3)), urea can be fed to the carbamate production process without melting the urea, and therefore dimerization of urea due to the heating can be suppressed, and the first biuret compound can be reduced.

Then, by reducing the first biuret compound in the first biuret compound reduction process, production of the disubstituted benzoyleneurea and a derivative thereof can be reduced, and therefore toluenedicarbamate can be produced with excellent efficiency, and also residues (solid content) obtained as by-products can be reduced.

The first biuret compound content reduced as described above is, for example, 40 mol or less, preferably 30 mol or less, more preferably 20 mol or less, and usually 0.01 mol or more relative to 100 mol of toluenediamine.

When the first biuret compound content is the above-described upper limit or less, production of the disubstituted benzoyleneurea and a derivative thereof can be reduced, and as a result, toluenedicarbamate can be produced with excellent efficiency.

[Second Biuret Compound Reduction Process]

As an example of the reaction pathway, in which the second biuret compound represented by formula (12A) above is produced as the intermediate from the above-described raw material components and further the disubstituted benzoyleneurea and a derivative thereof are produced from the second biuret compound, a reaction pathway represented by formula (18A) below may be used.

[Chemical Formula 15]

(18A)

-continued (5)
(10)

In such a reaction, urea is allowed to react with alcohol to produce N-unsubstituted carbamic acid ester. Then, by addition of urea to the obtained N-unsubstituted carbamic acid ester, the second biuret compound is produced, and by addition of toluenediamine to the second biuret compound, the disubstituted benzoyleneurea and a derivative thereof are produced.

Furthermore, as an example of the reaction pathway, in which the second biuret compound represented by formula (12B) above is produced as an intermediate from the above-described raw material components and further the disubstituted benzoyleneurea and a derivative thereof are produced from the second biuret compound, a reaction pathway represented by formula (18B) below may be used:

[Chemical Formula 16]

(18B)

-continued

To suppress such a reaction, addition of urea to the N-unsubstituted carbamic acid ester is suppressed to reduce the production of the second biuret compound.

Thus, in the second biuret compound reduction process, in the above-described N-unsubstituted carbamic acid ester production process, urea is allowed to react with alcohol in the presence of a metal-containing compound.

Examples of the metal-containing compound include the above-described catalysts, preferably, $Zn(OSO_2CF_3)_2$ (also known as: $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc p-toluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

These metal-containing compounds may be used singly or in a combination of two or more.)

The amount of the metal-containing compound relative to 1 mol of urea is, for example, 0.000001 to 0.1 mol, preferably 0.00005 to 0.05 mol.

When such a metal-containing compound is used, selectivity for reaction between urea and alcohol can be increased. Therefore, reaction between ureas themselves and addition of urea to the N-unsubstituted carbamic acid ester are suppressed, allowing reduction of the second biuret compound production.

Furthermore, to reduce the second biuret compound production in the N-unsubstituted carbamic acid ester production process, the reaction temperature of urea and alcohol is set to, for example, 200° C. or less, preferably 180° C. or less, and usually 140° C. or more.

Then, by reducing the second biuret compound by the second biuret compound reduction process, production of the disubstituted benzoyleneurea and a derivative thereof can be reduced, and therefore toluenedicarbamate can be produced with excellent efficiency, and further residues (solid content) obtained as by-products can be reduced.

The second biuret compound content reduced as described above is, for example, 40 mol or less, preferably 30 mol or less, more preferably 20 mol or less, and usually 0.01 mol or more relative to 100 mol of toluenediamine.

When the second biuret compound content is the above-described upper limit or less, production of the disubstituted benzoyleneurea and a derivative thereof can be reduced, and as a result, toluenedicarbamate can be produced with excellent efficiency.

[Third Biuret Compound Reduction Process]

As an example of the reaction pathway, in which the third biuret compound represented by formula (14) above or formula (15) above is produced as an intermediate from the above-described raw material components and further the disubstituted benzoyleneurea and a derivative thereof are produced from the third biuret compound, a reaction pathway represented by formula (19) below may be used:

[Chemical Formula 17]

That is, in this reaction, after urea or N-unsubstituted carbamic acid ester is added to toluenediamine, urea or N-unsubstituted carbamic acid ester is further added thereto to produce the third biuret compound, and by eliminating the urea or alcohol from the third biuret compound, the disubstituted benzoyleneurea and a derivative thereof are produced.

Furthermore, the reaction pathway, in which the above-described third biuret compound is produced as an intermediate from the above-described raw material components and further the disubstituted benzoyleneurea and a derivative thereof are produced from the third biuret compound, is not limited to the reaction pathway represented by formula (19) above, and examples thereof also include the following reaction pathways: the reaction pathway (in which the third biuret compound represented by formula (14) above is produced as an intermediate) of formula (17) above, and the reaction pathways (in which the third biuret compound represented by formula (15) above is produced as an intermediate) of formula (18A) above and the above-described formula (18B).

Furthermore, although the reaction pathway is not shown, in the reaction between toluenediamine, urea and/or N-unsubstituted carbamic acid ester, and alcohol, for example, by dimerization of the product obtained by addition of urea to toluenediamine, the biuret compound represented by formula (16) above is produced.

Thus, in the third biuret compound reduction process, to reduce these third biuret compounds, for example, (1) in the carbamate production process, from the reaction system, ammonia by-produced by the reaction is reduced.

Figure 2:
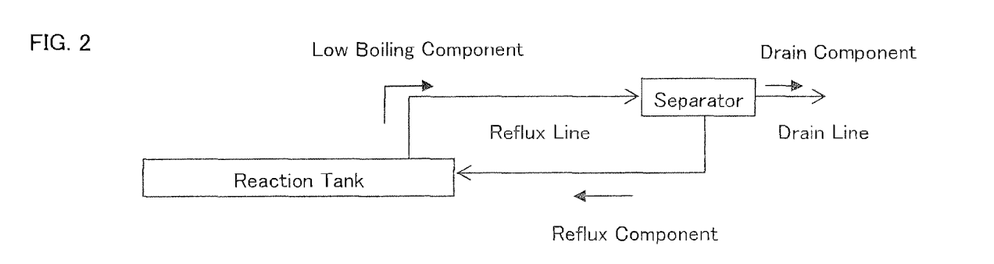
FIG. 2 is a schematic view illustrating an embodiment of a carbamate production process, when a third biuret compound reduction process is included.

FIG. 2 is a schematic view illustrating an embodiment of a carbamate production process, when a third biuret compound reduction process is included.

As shown in FIG. 2, when the carbamate production process is performed in a reaction apparatus including a reaction tank, a reflux line for refluxing the low boiling component (the above-described low boiling component, to be specific, excess (unreacted) alcohol, excess (unreacted) urea and/or N-unsubstituted carbamic acid ester, carbonate, etc.) drained from the reaction tank, and a separator provided in the reflux line for separating a reflux component from a drain component, examples of the method for reducing ammonia include:

(a) purging the reaction tank with nitrogen.

To purge the reaction tank with nitrogen, a nitrogen inlet line is connected to the reaction tank and nitrogen gas is introduced from the nitrogen inlet line to the reaction tank so that the low boiling component is purged from the reaction tank to the reflux line.

Other examples of the method also include:

(b) using a condenser as the separator, and setting the temperature of the condenser to, for example, 40° C. or more, preferably 50° C. or more to suppress the condensation of ammonia.

This allows a decrease in the ammonia concentration in the reflux component.

Other examples of the method also include:

(c) using a distiller as the separator, distillation is performed so that the ammonia amount contained in the drain component is larger relative to the ammonia amount contained in the reflux component.

This allows a decrease in the ammonia concentration in the reflux component.

These methods for reducing ammonia can be used singly or in a combination of two or more.

By reducing ammonia in this manner, the raw material components are preferentially used for the production of toluenedicarbamate (formula (8) above), and use of the raw material components for production of the above-described third biuret compound (including reactions producing the above-described first biuret compound and second biuret compound) can be suppressed, and therefore the third biuret compound can be reduced.

Furthermore, in the third biuret compound reduction process, in addition to the reduction of ammonia, for example, (2) in the reaction between toluenediamine, urea and/or N-unsubstituted carbamic acid ester, and alcohol, the reaction temperature is set to 160° C. or more, preferably 180° C. or more, more preferably 190° C. or more.

When the reaction temperature is set to the above-described lower limit or more, production of the third biuret compound can be suppressed.

Furthermore, in the third biuret compound reduction process, for example, (3) in the reaction between toluenediamine, urea and/or N-unsubstituted carbamic acid ester, and alcohol, 2 mol or more, preferably 2.5 mol or more of alcohol relative to 1 mol of toluenediamine can be fed.

When the above-described amount of alcohol is fed, further addition of urea or N-unsubstituted carbamic acid ester can be suppressed after addition of urea or N-unsubstituted carbamic acid ester to toluenediamine, and addition of alcohol is allowed.

Then, by allowing addition of alcohol after addition of urea or N-unsubstituted carbamic acid ester to toluenediamine, production of the third biuret compound can be suppressed, and this allows reaction of the path represented by formula (8) above, and acceleration of the production of toluenedicarbamate.

The third biuret compound content (total amount) reduced as described above relative to 100 mol of toluenediamine is, for example, 40 mol or less, preferably 30 mol or less, more preferably, 20 mol or less, and usually 0.01 mol or more.

When the third biuret compound content is the above-described upper limit or less, production of the disubstituted benzoyleneurea and a derivative thereof can be reduced, and as a result, toluenedicarbamate can be produced at excellent efficiency.

Thus produced toluenedicarbamate contains, as impurity, 0.01 to 10 mol, preferably 0.01 to 5 mol of the disubstituted benzoyleneurea and a derivative thereof relative to 100 mol of toluenedicarbamate, wherein the disubstituted benzoyleneurea is represented by formula (1) below and has a methyl group and an amino group:

[Chemical Formula 18]

(1)

In formula (1) above, the amino group (H$_2$N—) is preferably at 5 or 7 position, and the methyl group (H$_3$C—) is preferably at 6 or 8 position.

That is, examples of the above-described disubstituted benzoyleneurea and a derivative thereof include, to be more specific, 7-amino-6-methyl-1,2,3,4-tetrahydroquinazoline-2,4-dione, 5-amino-6-methyl-1,2,3,4-tetrahydroquinazoline-2,4-dione, 5-amino-8-methyl-1,2,3,4-tetrahydroquinazoline-2,4-dione, and 7-amino-8-methyl-1,2,3,4-tetrahydroquinazoline-2,4-dione.

As described above, typically, when toluenediamine, urea and/or N-unsubstituted carbamic acid ester, and alcohol are allowed to react, while the raw material components produce toluenedicarbamate, the same raw material components also produce the disubstituted benzoyleneurea represented by formula (1) above; therefore, production efficiency of toluenedicarbamate is disadvantageously reduced.

However, such a method for producing toluenedicarbamate includes the benzoyleneurea reduction process, and therefore the disubstituted benzoyleneurea and a derivative thereof are reduced to 10 mol or less relative to 100 mol of toluenedicarbamate.

Thus, with such a method for producing toluenedicarbamate, toluenedicarbamate can be produced with excellent efficiency.

Furthermore, such toluenedicarbamate is used, industrially, for example, for production of isocyanate. With the above-described method for producing toluenedicarbamate, the carbamate intermediate having an amino group is reduced, and therefore reaction between such a carbamate intermediate having an amino group and isocyanate can be reduced, and residues (solid content) obtained as by-products can be reduced.

The present invention includes a method for producing toluenediisocyanate in which toluenediisocyanate is produced by thermally decomposing toluenedicarbamate obtained by the above-described method for producing toluenedicarbamate.

In the method for producing toluenediisocyanate of the present invention, toluenedicarbamate is produced by the above-described method for producing toluenedicarbamate (toluenedicarbamate production process), and thereafter, the produced toluenedicarbamate is thermally decomposed to produce toluenediisocyanate (toluenediisocyanate production process).

To be more specific, in such a method for producing toluenediisocyanate, toluenedicarbamate obtained by the above-described method for producing toluenedicarbamate is thermally decomposed, to produce toluenediisocyanate represented by formula (20) below corresponding to the above-described toluenediamine;

[Chemical Formula 19]

(20)

and
alcohol represented by the general formula (21) below, which is a by-product:

R—OH (21)

(where R is as defined for R in formula (5) above).

Examples of the toluenediisocyanate include 2,4-toluenediisocyanate, 2,6-toluenediisocyanate, or their mixtures, in accordance with the raw material component toluenedicarbamate (and also its raw material component toluenediamine).

There is no particular limitation on the thermal decomposition. Any known decomposition method such as a liquid phase method or a vapor phase method can be used.

In the vapor phase method, the toluenediisocyanate and alcohol produced by the thermal decomposition can be separated from a gaseous product mixture by fractional condensation. In the liquid phase method, the toluenediisocyanate and alcohol produced by the thermal decomposition can be separated, for example, by distillation or using a solvent and/or inert gas as a support substance.

As the thermal decomposition, a liquid phase method is preferable from the viewpoint of workability.

In such a method, the toluenedicarbamate is thermally decomposed preferably in the presence of an inert solvent.

The inert solvent is not particularly limited as long as, at least, it dissolves the toluenedicarbamate, is inert to the toluenedicarbamate and toluenediisocyanate, and remains unreacted (i.e., stable) during the thermal decomposition. For efficient thermal decomposition reaction, the inert solvent preferably has a higher boiling point than that of the toluenediisocyanate to be produced.

As such an inert solvent, aromatic hydrocarbons may be used.

Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237-340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 241° C.), 1-chloronaphthalene (boiling point: 263° C.), 2-chloronaphthalene (boiling point: 264-266° C.), triphenylmethane (boiling point: 358 to 359° C. (754 mmHg)), 1-phenylnaphthalene (boiling point: 324-325° C.), 2-phenylnaphthalene (boiling point: 357-358° C.), and biphenyl (boiling point: 255° C.).

These solvents are also available as commercially available products, and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.), Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 2H (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove manufactured by Matsumura Oil Co., Ltd.); and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KSK-OIL 280 (aromatic hydrocarbon, boiling point: 303° C.) (hereinabove manufactured by Soken Tecnix Co., Ltd.).

Furthermore, examples of the inert solvent include esters (e.g., dioctyl phthalate, didecyl phthalate, and didodecyl phthalate) and aliphatic hydrocarbons which are commonly used as a heat transfer medium.

These inert solvents can be used singly or in a combination of two or more.

The amount of the inert solvent relative to 1 part by mass of toluenedicarbamate is in the range of 0.001 to 100 parts by mass, preferably 0.01 to 80 parts by mass, more preferably 0.1 to 50 parts by mass.

In the thermal decomposition, for example, the inert solvent is blended with the toluenedicarbamate, and the blended toluenedicarbamate is thermally decomposed. Thereafter, the inert solvent is separated and recovered, and then again can be blended with the toluenedicarbamate in the thermal decomposition.

Since the thermal decomposition reaction of the toluenedicarbamate in the liquid phase method is a reversible reaction, preferably, the toluenedicarbamate is thermally decomposed and, to suppress the reverse reaction (i.e., the urethane-forming reaction between the toluenediisocyanate represented by above-described formula (20) and alcohol represented by formula (21) above) to the thermal decomposition reaction, at the same time, the toluenediisocyanate represented by formula (20) above and/or the alcohol represented by above-described formula (21) are drawn out of the reaction mixture (decomposition solution) by a known method to be separated.

Preferable reaction conditions for the thermal decomposition reaction include reaction conditions in which the toluenedicarbamate can be thermally decomposed in an excellent manner, and at the same time, the toluenediisocyanate (formula (20) above) and alcohol (formula (21) above) produced by the thermal decomposition evaporate, whereby the toluenedicarbamate and toluenediisocyanate fail to reach equilibrium, and further, a side reaction such as polymerization of toluenediisocyanate is suppressed.

As the reaction conditions, more specifically, the thermal decomposition temperature is usually 350° C. or lower, preferably from 80 to 350° C., or more preferably from 100 to 300° C. At a thermal decomposition temperature lower than 80° C., a practical reaction rate may not be obtained. On the other hand, at a thermal decomposition temperature higher than 350° C., an undesired side reaction such as polymerization of toluenediisocyanate may occur. The pressure during the thermal decomposition reaction is preferably a pressure for allowing the alcohol produced to be vaporized at the thermal decomposition reaction temperature specified above. For practical use, the pressure is preferably in the range of 0.133 to 90 kPa in terms of equipment and utilities.

In this method, a catalyst may be added if necessary.

Although it depends on the kind of catalyst, the catalyst may be added at any time such as during the above-described reaction, before or after distillation and separation after the reaction, and before or after separation of the toluenedicarbamate.

As the catalyst used for the thermal decomposition, at least one metal selected from the group consisting of Sn, Sb, Fe, Co, Ni, Cu, Cr, Ti, Pb, Mo, and Mn, or a metallic compound thereof such as oxide, halide, carboxylate, phosphate, and organometallic compound, used for the urethane-forming reaction of a toluenediisocyanate and a hydroxyl group is used. Among them, Fe, Sn, Co, Sb, and Mn are preferably used in the thermal decomposition because they exhibit the effect of suppressing the production of a by-product.

Examples of the metallic catalyst of Sn include tin oxide, tin chloride, tin bromide, tin iodide, tin formate, tin acetate, tin oxalate, tin octylate, tin stearate, tin oleate, tin phosphorate, dibutyltin dichloride, dibutyltin dilaurate, and 1,1,3,3-tetrabutyl-1,3-dilauryloxydistannoxane.

Examples of the metallic catalysts of Fe, Co, Sb, and Mn include acetate, benzoate, naphthenate, and acetylacetonate thereof.

The blending amount of the catalyst is in the range of 0.0001 to 5% by mass, or preferably 0.001 to 1% by mass, per the reaction solution, as a metal or a compound thereof.

The thermal decomposition reaction can be carried out by a batch reaction process in which the toluenedicarbamate, the catalyst, and the inert solvent are added by a batch, or by a continuous reaction process in which the tolylene dicarbamate is added into the inert solvent containing the catalyst under reduced pressure.

In the thermal decomposition, a toluenediisocyanate and an alcohol are produced and, for example, allophanate, amines, urea, carbonate, carbamate, and carbon dioxide may also be produced by a side reaction in some cases. Therefore, if necessary, the toluenediisocyanate thus produced is purified by a known method.

The alcohol (formula (21) above) obtained by the thermal decomposition is separated and recovered, and thereafter preferably used as a raw material component for the toluenedicarbamate-forming reaction.

With such a method for producing toluenediisocyanate, the above-described method for producing toluenedicarbamate is used, and therefore production of the disubstituted benzoyleneurea and a derivative thereof is reduced, thus the blockage of the production system is suppressed, and isocyanate production with excellent yield can be achieved.

The method for producing toluenedicarbamate and method for producing toluenediisocyanate are described above, and in such a method for producing toluenedicarbamate and a method for producing toluenediisocyanate, as necessary, at an appropriate position, a pretreatment step such as a dehydration step, an intermediate step, and a post-treatment step such as a distillation step, filtering step, purifying step, and recovery step can be included.

EXAMPLES

Next, the present invention will be described in further detail by way of Examples and Comparative Examples, but the present invention is not limited thereto.

In Examples and Comparative Examples, determination of the components is based on the HPLC measurement conditions below.

1) Apparatus and Measurement Conditions
Apparatus: Shimadzu HPLC (SCL-10A, DGU-12A, LC-10AD, RID-10A, SPD-10A)
Column: WAKOSIL5C18 (4.6 mmID×250 mm, 5.0 μm)
Mobile Phase: acetonitrile/70 wtppm aqueous solution of phosphoric acid=85/15v/v
Flow velocity: 0.8 ml/min
Column temperature: 40° C.
Injection Amount: 10 μL
Detector: UV/vis (detection wavelength 254 nm), RI 2) Analysis

A sample was diluted with acetonitrile to about 1:100, and subjected to analysis in the HPLC under the above-described conditions. The determination is carried out using reference solutions of 2,4-toluenedibutylcarbamate (2,4-TDCBu), 2,6-toluenedibutylcarbamate (2,6-TDCBu), 2,4-toluenedioctylcarbamate (2,4-TDCOc), and octyl carbamate (COE). For the disubstituted benzoyleneurea derivative represented by formula (22), and the disubstituted benzoyleneurea represented by formula (23), 2,4-TDCBu was used as reference; for the disubstituted benzoyleneurea derivative represented by formula (24), 2,4-TDCOc was used as reference; and for the second biuret compound (biuret OE) represented by formula (25) and the second biuret compound (biuret DOE) represented by (26), COE was used as reference. The determination was performed using a scaling factor of 1.

[Chemical Formula 20]

(22)

[Chemical Formula 21]

(23)

[Chemical Formula 22]

(24)

[Chemical Formula 23]

(25)

[Chemical Formula 24]

(26)

Example 1

2,4-TDA/Biuret-Containing Urea/Octanol

A 200 mL glass flask equipped with a reflux condenser, a gas-liquid separator, and a stirrer was charged with 12.0 g (0.10 mol) of 2,4-diaminotoluene (hereinafter 2,4-TDA), 73.0 g (0.56 mol) of 1-octanol, and also 0.202 g (0.50 mmol) of zinc p-toluenesulfonate as a catalyst. While the mixture was stirred at 500 rpm and a nitrogen gas was allowed to flow at 150 mL per minute, the temperature was increased to 210° C. After the temperature was allowed to reach 210° C., 17.8 g (0.29 mol) of a liquid urea, which is a urea melted at 140° C. for 40 minutes, was introduced thereto, and the mixture was allowed to react at a reaction temperature of 210° C. for 4 hours, thereby producing 88.1 g of a reaction solution.

The liquid urea introduced thereto was partially collected, and determined by a liquid chromatograph (RI detector). It was confirmed that 2.5 mol % of biuret was present. This is because the liquid urea underwent thermal hysteresis at 140° C. for 40 min, and partially reacted to produce biuret (first biuret compound). That is, it was confirmed that 17.0 g of urea, and 0.75 g of biuret was introduced into the reactor.

The reaction solution was partially collected and determined, and it was confirmed that 2,4-toluenedioctylcarbamate (2,4-bis(octyloxycarbonylamino) toluene, hereinafter referred to as TDCOe) was produced at a yield of 95.3 mol % relative to 2,4-TDA. Furthermore, it was confirmed that a disubstituted benzoyleneurea derivative represented by formula (24) above was produced at a yield of 2.9 mol % relative to 2,4-TDA, and that a disubstituted benzoyleneurea represented by formula (23) above was produced at a yield of 4.6 mol % relative to 2,4-TDA. This corresponds to 7.9 mol of disubstituted benzoyleneurea relative to 100 mol of 2,4-TDCOc.

Example 2

2,4-TDA/Urea/Octanol

A 200 mL glass flask equipped with a reflux condenser, a gas-liquid separator, and a stirrer was charged with 12.0 g (0.10 mol) of 2,4-TDA and 73.0 g (0.56 mol) of 1-octanol, and also 0.191 g (0.47 mmol) of zinc p-toluenesulfonate as a catalyst. While he mixture was stirred at 500 rpm and a nitrogen gas was allowed to flow at 150 mL per minute, the temperature was increased to 210° C. After the temperature was allowed to reach 210° C., 17.7 g (0.29 mol) of urea in the form of powder was introduced therein, and the mixture was allowed to react at a reaction temperature of 210° C. for 4 hours, thereby producing 88.3 g of a reaction solution.

The reaction solution was partially collected and determined, and it was confirmed that 2,4-TDCOc was produced at a yield of 96.4 mol % relative to 2,4-TDA. Furthermore, it was confirmed that a disubstituted benzoyleneurea derivative represented by formula (24) above was produced at a yield of 2.3 mol % relative to 2,4-TDA, and the disubstituted benzoyleneurea represented by formula (23) above was produced at a yield of 3.7 mol % relative to 2,4-TDA. This corresponds to 6.2 mol of disubstituted benzoyleneurea relative to 100 mol of 2,4TDCOc.

Example 3

2,4-TDA/Butyl Carbamate/Butanol

A 1 L SUS autoclave equipped with a pressure control valve, a reflux condenser, a gas-liquid separator, and a stirrer was charged with a mixture of 80.7 g (0.661 mol) of 2,4-TDA, 221 g (1.89 mol) of butyl carbamate, and 140 g (1.89 mol) of 1-butanol, and also 0.649 g (1.59 mmol) of zinc p-toluenesulfonate as a catalyst. While the mixture was stirred at 500 rpm with a nitrogen gas allowed to flow at 1 liter per minute, and the internal pressure was controlled to maintain the reaction temperature at 200° C. by the pressure control valve, the mixture was allowed to react for 10 hours to give 410 g of a reaction solution.

The reaction solution was partially collected and determined, and it was confirmed that 2,4-toluenedibutylcarbamate (2,4-bis(butyloxycarbonylamino) toluene, hereinafter referred to as TDCBu) was produced at a yield of 96.7 mol % relative to 2,4-TDA. Furthermore, it was confirmed that a disubstituted benzoyleneurea derivative represented by formula (22) above was produced at a yield of 0.59 mol % relative to 2,4-TDA, and that a disubstituted benzoyleneurea represented by formula (23) above was produced at a yield of 0.99 mol % relative to 2,4-TDA. This corresponds to 1.6 mol of disubstituted benzoyleneurea relative to 100 mol of 2,4TD-CBu.

Example 4

2,4-TDA/2,6-Diaminotoluene/Urea/Butanol

A 1 L SUS autoclave equipped with a pressure control valve, a reflux condenser, a gas-liquid separator, and a stirrer was charged with a mixture of 80.6 g (0.660 mol) of 2,4-TDA/2,6-diaminotoluene (hereinafter referred to as 2,6-TDA) with an isomer mixing ratio of 80/20 (hereinafter referred to as TDA-80), 113 g (1.89 mol) of urea, and 279 g (3.79 mol) 1-butanol at normal temperature, and also 0.644 g (1.58 mmol) of zinc p-toluenesulfonate as a catalyst. While the mixture was stirred at 500 rpm with a nitrogen gas allowed to flow at 1 L per minute, and the internal pressure was controlled to maintain the reaction temperature at 200° C. by the pressure control valve, the mixture was allowed to react for 6 hours to give 410 g of a reaction solution.

The reaction solution was partially collected and determined, and it was confirmed that 2,4-TDCBu was produced at a yield of 94.0 mol % relative to 2,4-TDA, and 2,6-TDCBu was produced at a yield of 88.8 mol % relative to 2,6-TDA. Furthermore, it was confirmed that a disubstituted benzoyleneurea derivative represented by formula (22) above was produced at a yield of 2.6 mol % relative to TDA-80 and the disubstituted benzoyleneurea represented by formula (23) above was produced at a yield of 5.0 mol % relative to TDA-80. This corresponds to 8.2 mol of disubstituted benzoyleneurea relative to 100 mol of a total of 2,4-TDCBu and 2,6-TDCBu.

Example 5

2,4-TDA/Urea/Butanol

1) Production of 2,4-Toluenedibutylcarbamate

A 1 L SUS autoclave equipped with a pressure control valve, a reflux condenser, a gas-liquid separator, and a stirrer was charged with a mixture of 80.6 g (0.660 mol) of 2,4-TDA, 113 g (1.89 mol) of urea, and 279 g (3.79 mol) of 1-butanol at normal temperature, and also 0.643 g (1.58 mmol) of zinc p-toluenesulfonate as a catalyst. While the mixture was stirred at 500 rpm with a nitrogen gas allowed to flow at 150 mL per minute, and the internal pressure was controlled to maintain the reaction temperature at 200° C. by the pressure control valve, the mixture was allowed to react for 4 hours, thereby producing a reaction solution of 410 g.

The reaction solution was partially collected and determined, and it was confirmed that 2,4-TDCBu was produced at a yield of 91.9 mol % relative to 2,4-TDA. Furthermore, it was confirmed that a disubstituted benzoyleneurea derivative represented by formula (22) above was produced at a yield of 1.4 mol % relative to 2,4-TDA, and the disubstituted benzoyleneurea represented by formula (23) above was produced at a yield of 4.7 mol % relative to 2,4-TDA. This corresponds to 6.6 mol of disubstituted benzoyleneurea relative to 100 mol of 2,4-TDCBu.

2) Production of Toluenediisocyanate 2-1) A Process of Removing Unreacted Component and by-Products from the Reaction Solution Obtained as Described Above was Performed.

A 500 mL glass four-neck flask equipped with a stirrer and a condenser tube was charged with the above-described reaction solution, and while the reaction solution was stirred at 230 rpm, the pressure in the flask was reduced to 2 kPa with a vacuum pump. The temperature in the flask was increased to 100° C. with circulation water of 25° C. flowing through the condenser tube, so as to distill off the low boiling component containing butanol as a main component. With the $^1$HNMR measurement, it was confirmed that no compound containing an aromatic ring is present in the low boiling component.

Thereafter, the temperature of the circulation water was set again to 80° C., and the temperature of the flask was increased to 180° C. to distill off a medium boiling point compound, thereby producing 210 g of brown carbamate concentrate. Meanwhile, it was confirmed with $^1$HNMR measurement that the distillate contained butyl carbamate as a main component, and that no compound containing an aromatic ring was present.

The carbamate concentrate was partially collected, and determined by liquid chromatograph (UV detector (254 nm) and RI detector). It was confirmed that 90 mass % of 2,4-TDCBu was present.

2-2) Production of Isocyanate by Thermal Decomposition of Concentrate

A 1000 mL glass separable flask equipped with a thermometer, a stirrer, and a rectifying column having a reflux pipe at its upper portion was charged with 200 g (0.56 mol of 2,4-TDCBu) of the concentrate obtained as described above, and 200 g of Barrel Process Oil B-05 (manufactured by Matsumura Oil Co., Ltd.) as a solvent, and while the mixture was stirred at 300 rpm, the pressure in the flask was reduced to 10 kPa with a vacuum pump.

As heating was started while circulation water of 90° C. was allowed to flow in the reflux pipe, the column top temperature increased at around 220° C., and 2,4-tolylenediisocyanate (hereinafter referred to as 2,4-TDI) started to condense in the reflux pipe. Thus, the reflux ratio was set to 15 (=reflux 30 seconds/distillation 2 seconds), thereby distilling off 2,4-TDI. The column top temperature increased after 6 hours from the start of the distillation, and thus the heating and pressure reduction were terminated, thereby producing 111 g of a distillate.

The distillate was partially collected and determined by liquid chromatograph (UV detector (254 nm) and RI detector). The result showed that the distillate contained 81 mass % (0.52 mol) of 2,4-TDI, and the compound other than 2,4-TDI was mostly the solvent, i.e., Barrel Process Oil B-05, and disubstituted benzoyleneurea derivative represented by formula (22) above and the disubstituted benzoyleneurea represented by formula (23) above were not detected. As a result, the yield of the recovered 2,4-TDI relative to 2,4-TDCBu in the thermal decomposition was 93 mol % (86 mol % calculated from 2,4-TDA).

Meanwhile, the reaction solution was cooled to 120° C., and thereafter, separated into filtrate and residue by hot filtration with 5A filter paper. The residue was washed with acetone and dried, recovering 4 g of a yellowish brown residue. The production rate of tar relative to the reaction solution concentrate was 2 mass %.

Comparative Example 1

1) Synthesis of Octyl Carbamate

A 1000 mL glass flask equipped with a reflux condenser, a gas-liquid separator, and a stirrer was charged with 522.4 g (4.01 mol) of 1-octanol and 60.07 g (1.00 mol) of urea. While the mixture was stirred at 500 rpm and nitrogen gas was allowed to flow at 30 mL per minute, the mixture was allowed to react at 165° C. After 90 min, 52.1 g (0.87 mol) of urea was added, and after 120 min, 49.34 g (0.82 mol) of urea was added, and the mixture was allowed to react at a reaction temperature of 165° C.

The reaction was terminated after 6 hours, and after distilling off the unreacted octanol by evaporation, 400 g of sample, which is solid at normal temperature, was recovered by simple distillation under reduced pressure.

The solid was partially collected, and determined by liquid chromatograph (RI detector). It was confirmed that the solid contained 81 mol % of octyl carbamate, 13 mol % of the second biuret compound (biuret OE) represented by formula (25) above, and 6 mol % of the second biuret compound (biuret DOE) represented by formula (26).

2) Reaction of 2,4-TDA/Biuret Compound-Containing Octyl Carbamate/Octanol

A 200 mL glass flask equipped with a reflux condenser, a gas-liquid separator, and a stirrer was charged with 9.52 g (0.08 mol) of 2,4-TDA and 50.63 g (0.39 mol) of 1-octanol. While the mixture was stirred at 500 rpm and nitrogen gas was allowed to flow at 150 mL per minute, the temperature was increased to 200° C. After the temperature reached 200° C., 67.27 g (0.39 mol) of the octyl carbamate obtained as described above containing 19 mol % of biuret compound was added to the mixture. The second biuret compound added corresponds to 95 mol relative to 100 mol of 2,4-TDA. The mixture was allowed to react at a reaction temperature of 200° C. for 4 hours, thereby producing 119.2 g of a reaction solution.

The reaction solution was partially collected, and determined by liquid chromatograph (UV detector (254 nm) and RI detector). The yields (relative to 2,4-TDA) confirmed were as follows: 77.6 mol % of 2,4-TDCOc; 2.4 mol % of the disubstituted benzoyleneurea derivative represented by formula (24) above; and 17.8 mol % of the disubstituted benzoyleneurea represented by formula (23) above. This corresponds to 26 mol of the disubstituted benzoyleneurea relative to 100 mol of 2,4-TDCOc. It was confirmed that when the biuret compound as described above is present at a high proportion, the disubstituted benzoyleneurea is produced at a very high rate.

Comparative Example 2

A 1 L SUS autoclave equipped with a pressure control valve, a reflux condenser, a gas-liquid separator, and a stirrer was charged with a mixture of 80.6 g (0.660 mol) of 2,4-TDA, 113 g (1.89 mol) of urea, and 279 g (3.79 mol) of 1-butanol at normal temperature, and also 0.643 g (1.58 mmol) of zinc p-toluenesulfonate as a catalyst. While the mixture was stirred at 500 rpm and nitrogen gas was allowed to flow at 1 L per minute, first, the mixture was allowed to react for 6 hours while the internal pressure was controlled with the pressure control valve so as to keep the reaction temperature to 100° C., and after the mixture was further allowed to react at 130° C. for 3 hours, the temperature was increased to 200° C. to allow further reaction for 6 hours to terminate the reaction, thereby producing 410 g of a reaction solution.

The reaction solution was partially collected and determined, and it was confirmed that 2,4-TDCBu was produced at a yield of 86.9 mol % relative to 2,4-TDA. Furthermore, it was confirmed that a disubstituted benzoyleneurea derivative represented by formula (22) above was produced at a yield of 2.5 mol % relative to 2,4-TDA, and the disubstituted benzoyleneurea represented by formula (23) above was produced at a yield of 7.3 mol % relative to 2,4-TDA. This corresponds to 11.3 mol of the disubstituted benzoyleneurea relative to 100 mol of 2,4-TDCBu.

Comparative Example 3

1) Production of 2,4-Toluenedibutylcarbamate

A 1 L SUS autoclave equipped with a pressure control valve, a reflux condenser, a gas-liquid separator, and a stirrer was charged with a mixture of 80.6 g (0.660 mol) of 2,4-TDA, 113 g (1.89 mol, Wako Pure Chemical Industries, Ltd., purity>99.0%) of urea, and 279 g (3.79 mol) of 1-butanol, and also 0.644 g (1.58 mmol) of zinc p-toluenesulfonate as a catalyst. The mixture was allowed to react for 4 hours without the nitrogen gas flow while stirring at 500 rpm, and controlling the internal pressure with the pressure control valve so as to keep the reaction temperature to 200° C., thereby producing 410 g of a reaction solution.

The reaction solution was partially collected and determined, and it was confirmed that 2,4-TDCBu was produced at a yield of 65.0 mol % relative to 2,4-TDA. Furthermore, it was confirmed that a disubstituted benzoyleneurea derivative represented by formula (22) above was produced at a yield of 9.3 mol % relative to 2,4-TDA, and the disubstituted benzoyleneurea represented by formula (23) above was produced at a yield of 18.3 mol % relative to 2,4-TDA. This corresponds to 42.5 mol of the disubstituted benzoyleneurea relative to 100 mol of 2,4-TDCBu. This is probably because the nitrogen gas flow was not used, ammonia did not escape from the system, and a large amount of biuret was produced in the system.

2) Production of Toluenediisocyanate 2-1) A Process of Removing Unreacted Component and by-Products from the Reaction Solution Obtained as Described Above was Performed.

A 500 mL glass four-neck flask equipped with a stirrer and a condenser tube was charged with the above-described reaction solution, and while the reaction solution was stirred at 230 rpm, the pressure in the flask was reduced to 2 kPa with a vacuum pump. The temperature in the flask was increased to 100° C. with circulation water of 25° C. flowing through the condenser tube, so as to distill off the low boiling component containing butanol as a main component. With the $^1$HNMR measurement, it was confirmed that no compound containing an aromatic ring is present in the low boiling component. Thereafter, the temperature of the circulation water was set again to 80° C., and the temperature of the flask was increased to 180° C. to distill off a medium boiling point compound, thereby producing 206 g of a brown carbamate concentrate. Meanwhile, it was confirmed with the $^1$HNMR measurement that the distillate contained butyl carbamate as a main component, and that no compound containing an aromatic ring was present. The carbamate concentrate was partially collected, and determined by liquid chromatograph (UV detector (254 nm) and RI detector). It was confirmed that 60 mass % of 2,4-TDCBu was present.

2-2) Production of Isocyanate by Thermal Decomposition of Concentrate

A 1000 mL glass separable flask equipped with a thermometer, a stirrer, and a rectifying column having a reflux pipe at its upper portion was charged with 200 g (0.37 mol as 2,4-TDC) of the reaction solution concentrate obtained by reduced pressure distillation of the light boiling component, and 200 g of Barrel Process Oil B-05 (manufactured by Matsumura Oil Co., Ltd.) as a solvent, and while the mixture was stirred at 300 rpm, the pressure in the flask was reduced to 10 kPa with a vacuum pump. As heating was started while circulation water of 90° C. was allowed to flow in the reflux pipe, the column top temperature increased at around 220° C., and 2,4-tolylenediisocyanate (hereinafter referred to as 2,4-TDI) started to condense in the reflux pipe. Thus, the reflux ratio was set to 15 (=reflux 30 sec/distillation 2 seconds), thereby distilling off 2,4-TDI. The column top temperature increased after 2 hours from the start of the distillation, and thus the heating and pressure reduction were terminated, thereby producing 60 g of a distillate. The distillate was partially collected and determined by liquid chromatograph (UV detector (254 nm) and RI detector). The result showed that the distillate contained 70 mass % (0.24 mol) of 2,4-TDI, and the compound other than 2,4-TDI was mostly the solvent, i.e., the Barrel Process Oil B-05, and the disubstituted benzoyleneurea derivative represented by formula (22) above and the disubstituted benzoyleneurea represented by formula (23) above were not detected. As a result, the yield of the recovered 2,4-TDI relative to 2,4-TDCBu in the thermal decomposition was 65 mol % (42 mol % calculated from 2,4-TDA), which was a very low value.

Meanwhile, the reaction solution was cooled to 120° C., and thereafter, separated into filtrate and residue by hot filtration with 5A filter paper. The residue was washed with acetone and dried, recovering 64 g of a yellowish brown residue. It was confirmed that the production rate of tar relative to the reaction solution concentrate was 32 mass %, i.e., the environment easily produced tar.

As described above, it was confirmed that when the carbamate compound containing a large amount of disubstituted benzoyleneurea is thermally decomposed, not only the yield of isocyanate is reduced, but also the production rate of tar became significantly high.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

A method for producing toluenedicarbamate of the present invention, a method for producing toluenediisocyanate, and toluenedicarbamate can be used as a raw material and a production method for various fine chemicals.

The invention claimed is:
1. A method for producing toluenedicarbamate comprising:
  a carbamate production process of producing toluenedicarbamate by reaction between toluenediamine, urea and/or N-unsubstituted carbamic acid ester, and alcohol; and
  a benzoyleneurea reduction process of reducing a disubstituted benzoyleneurea and a derivative thereof to 10 mol or less relative to 100 mol of toluenedicarbamate, wherein the disubstituted benzoyleneurea is represented by formula (1) below and has a methyl group and an amino group:

[Chemical Formula 1]

(1)

wherein the disubstituted benzoyleneurea derivative is represented by formula (10)

(10)

where R represents an alkyl group or an aryl group which may have a substituent.

2. The method for producing toluenedicarbamate according to claim 1, wherein the benzoyleneurea reduction process comprises a biuret compound reduction process of reducing a biuret compound represented by formula (2) below to 40 mol or less relative to 100 mol of toluenediamine:

$$X_1-CO-NH-CO-X_2 \quad (2)$$

where $X_1$ and $X_2$ may be the same or different from each other, and represent an amino group, an alkoxy group, or an N-(aminotoluoyl)amino group.

3. The method for producing toluenedicarbamate according to claim 2, wherein the biuret compound reduction process comprises a first biuret compound reduction process of reducing a first biuret compound represented by formula (2) above where $X_1$ and $X_2$ are amino groups.

4. The method for producing toluenedicarbamate according to claim 3, further comprising a urea feeding process of feeding urea to the carbamate production process,
wherein in the first biuret compound reduction process,
when the urea feeding process includes a fluid feeding process, in which urea is melted by heating to be in a fluid state, and to be fed to the carbamate production process, the time after the melting of urea to the completion of its feeding is set to within 2 hours,
in the urea feeding process, urea is fed as a slurry to the carbamate production process, or
in the urea feeding process, urea is fed in a solid state to the carbamate production process.

5. The method for producing toluenedicarbamate according to claim 2, wherein the biuret compound reduction process comprises a second biuret compound reduction process of reducing a second biuret compound represented by formula (2) above where $X_1$ is an amino group or an alkoxy group and $X_2$ is an alkoxy group.

6. The method for producing toluenedicarbamate according to claim 5, further comprising an N-unsubstituted carbamic acid ester production process of producing N-unsubstituted carbamic acid ester by reaction between urea and alcohol,
wherein in the second biuret compound reduction process, urea and alcohol are allowed to react in the presence of a metal-containing compound in the N-unsubstituted carbamic acid ester production process.

7. The method for producing toluenedicarbamate according to claim 2, wherein the biuret compound reduction process comprises a third biuret compound reduction process of reducing a third biuret compound represented by formula (2) above where $X_1$ is an N-(aminotoluoyl)amino group, and $X_2$ is any of an amino group, an alkoxy group, and an N-(aminotoluoyl)amino group.

8. The method for producing toluenedicarbamate according to claim 7, wherein in the third biuret compound reduction process,
in the carbamate production process,
ammonia by-produced in the reaction is reduced from the reaction system,
the reaction temperature is set to 160° C. or more, or
2 mol or more of alcohol relative to 1 mol of toluenediamine is fed.

9. The method for producing toluenedicarbamate according to claim 8, wherein the carbamate production process is performed in a reaction apparatus including a reaction tank, a reflux line for refluxing a low boiling component drained from the reaction tank, and a separator provided in the reflux line for separating a reflux component and a drain component, and
when the third biuret compound reduction process is a process of reducing ammonia by-produced in the reaction from the reaction system in the carbamate production process,
the reaction tank is purged with nitrogen,
a condenser is used as the separator, and the temperature of the condenser is set to 40° C. or more to suppress condensation of ammonia, or
a distiller is used as the separator, and distillation is performed so that the amount of ammonia contained in the drain component is larger than the amount of ammonia contained in the reflux component.

10. The method for producing toluenediisocyanate, comprising:
a toluenedicarbamate producing process, and
a toluenediisocyanate producing process of thermally decomposing the produced toluenedicarbamate,
wherein the toluenedicarbamate producing process comprises:
a carbamate production process of producing toluenedicarbamate by reaction between toluenediamine, urea, and/or N-unsubstituted carbamic acid ester, and alcohol; and
a benzoyleneurea reduction process of reducing a disubstituted benzoyleneurea and a derivative thereof to 10 mol or less relative to 100 mol of toluenedicarbamate,
wherein the disubstituted benzoyleneurea is represented by formula (1) below and has a methyl group and an amino group:

[Chemical Formula 1]

(1)

wherein the disubstituted benzoyleneurea derivative is represented by formula (10)

(10)

where R represents an alkyl group or an aryl group which may have a substituent.

11. A toluenedicarbamate comprising:

as an impurity, 0.01 to 10 mol of a disubstituted benzoyleneurea and a derivative thereof relative to 100 mol of toluenedicarbamate, wherein the disubstituted benzoyleneurea is represented by formula (1) below and has a methyl group and an amino group:

[Chemical Formula 2]

(1)

wherein the disubstituted benzoyleneurea derivative is represented by formula (10)

(10)

where R represents an alkyl group or an aryl group which may have a substituent.

* * * * *